United States Patent [19]
Timmermeyer, Sr. et al.

[11] Patent Number: 5,498,637
[45] Date of Patent: Mar. 12, 1996

US005498637A

[54] SUN RISE LOTION

[76] Inventors: Ronald E. Timmermeyer, Sr., P.O. Box 2547, Van Nuys, Calif. 91404; Susan K. Zarp, 6549 Balcom Ave., Reseda, Calif. 91335

[21] Appl. No.: 321,544

[22] Filed: Oct. 12, 1994

[51] Int. Cl.⁶ ............................. A61K 7/40; A61K 7/48
[52] U.S. Cl. .................... 424/195.1; 424/59; 424/62; 514/847
[58] Field of Search ................. 424/59, 62; 514/828, 514/938, 847

[56] References Cited

U.S. PATENT DOCUMENTS

| | | | |
|---|---|---|---|
| 624,925 | 5/1899 | Grapewine | 424/62 |
| 3,776,857 | 12/1973 | Linder | 514/938 |
| 3,919,430 | 11/1975 | Siegel | 514/938 |
| 4,125,603 | 11/1978 | Audibert et al. | 514/938 |
| 4,384,974 | 5/1983 | Guthauser | 514/938 |
| 4,776,976 | 10/1988 | Nakamura et al. | 514/938 |
| 4,816,271 | 3/1989 | Scaffidi | 514/938 |
| 5,165,917 | 7/1992 | Zabotto et al. | 514/938 |

OTHER PUBLICATIONS

Bennett, The Cosmetic Formulary, 1937, pp. 27, 28, 51, and 65.
Pharmaceutical Formulas, 1946, vol. II, pp. 52 and 117.

*Primary Examiner*—Dale R. Ore

[57] ABSTRACT

This invention relates to a method for moisturizing the skin with a natural product consisting of fresh lemon juice, extra virgin olive oil, and water.

1 Claim, No Drawings

SUN RISE LOTION

SUMMARY OF THE INVENTION

The nature of the invention is the combination of lemon juice, extra virgin olive oil and water. The substance of the invention is the extra virgin olive oil. The extra virgin olive oil, lemon juice and water are all natural substances that have been proven for centuries to be benefical to humanity. The medical field, health occupations, beauty and cosmetics industry, Aromatherapy, Herbalism and gourmet cooks, chefs, and lay people can and have continued to recognize these ingredients to enhance their lives. The lemon cleanses acid and dirt off of the skin while the extra virgin olive oil moisturizes the skin and brings it back to a smoother texture with a clean natural glow. The water cools and blends the combination of lemon and oil so that the mixture can be easily absorbed into the skin. Body skin, feet and elbows and the entire body skin will become smoother and softer.

The mixture can be sprayed on wood furniture as a means for cleaning or as a menas in cooking, marinating, frying, baking, steaming or as a menas in salads and blended with other cooking mixtures. The mixture can be drank without any harmful effects.

The composition of the ingredients, which contain specific measured quantities in relation to the whole: meaning, water, extra virgin olive oil and lemon juice are what provides the external softening, glowing and healthy clean skin apperance. The added useage of cooking, drinking it or cleaning wood furniture are other means of use.

The best mode of operation and gaining the most positive results are derived from the quantities of the ingredients in relation to one another and than combined to make the whole body lotion. The mixture is than best used from a spray bottle or can be used with the same effectiveness from a pour spout or cap type bottle. Size and ounces of bottle can increase or decrease. Shape of bottle can be changed.

DETAILED DESCRIPTION AND SPECIFICATION OF THE INVENTION

The invention is a combination of specific measured amounts of fresh lemon juice, extra virgin olive oil and water in relationship to one another. The invention is or can be used from either a spray bottle or a bottle with a pour cap or a pour spout.

Begin with the following items to mix the invention:

1. A medium sized fresh lemon
2. Extra Virgin Olive Oil
3. Tap water
4. Liquid measuring cup
5. Cutting board
6. Sharp cutting knife
7. Spray bottle that holds at least twenty ounces of liquid.

The twenty ounce bottle was used for the purpose of measuring amount used on a daily basis and length of time that the mixture appeared to keep a clean fresh consistancy.

The manner and process of making the same is as follows:

Place your cutting board and knife in front of you and place the liquid measuring cup to the outside center top of the cittomg board or to the right or left of the outside edge of cutting board.

Take the medium sized lemon and cut it in half. Take the one half of the lemon and cut that half into four quarters.

Take the liquid measuring cup and one quarter of the four quarters of the lemon that was cut from the one half of the lemon and squeeze it by hand into the measuring cup. Take the other two quarters making a total of three quarters of the four quarters of the original half of the lemon that will be used and squeez the juice from these two quarters into the liquid measuring cup. These three quarters squeesed of the one half will give you about one-half ounce of lemon juice.

Pour the extra virgin olive oil into the measuring cup on top of the lemon juice and increase to the liquid measure of two and one-third ounces, which means that the olive oil added is approximately one and five-sixths ounces.

Fill the liquid measuring cup with water and stir entire mixture. Pour the mixture into a twenty ounce spray bottle and than fill the spray bottle with tap water to the nineteen ounce level.

Occasionally shake the spray bottle while spraying the entire body. To use on the face, spray a small amount into the palm of one hand and rub palms together. Lightly spread over the face area. A soft towel can be used to blot face.

The body area can dry naturally and does not require any blotting or drying with a towel. After natural drying, place on clothes. There will be no residue left on body that will harm clothing.

Spray lotion or bottled lotion can also be rubbed into the body. Dry naturally or towel blot. Size and shape of bottle used can increase or decrease.

The formula for the spray lotion or bottled lotion is:

1. Three quarters of one-half of a lemon that has been cut into four quarters.
2. Approximately one and five-sixths ounces of extra virgin olive oil.
3. Approximately seventeen and one-sixth ounces of tap water.

The lotion can be sprayed or rubbed on and the quanity of the mixture can be adjusted to a light, medium or heavy texture. The lotion adds a healthy glow to the skin and with consistent use it continues to soften the texture of the skin.

When spraying the lotion the spray will not damage any surrounding items and if sprayed accidently on glass will only leave a film on the glass. It will not damage any items that it comes in contact with or on. The mixture can be used for cooking and can be drunk.

We claim:

1. A method of moisturizing the skin by spraying or splashing an effective amount of a body lotion consisting of Fresh squeezed lemon juice: ½ oz.

Extra virgin olive oil: 1 and ⅚ ozs.

Tap water: 17 and ⅙ ozs.

* * * * *